(12) United States Patent
Lau et al.

(10) Patent No.: US 9,144,421 B1
(45) Date of Patent: Sep. 29, 2015

(54) OPTIMIZATION OF ACOUSTIC WINDOW AND TARGET DEPTH FOR TRANSABDOMINAL ULTRASOUND TREATMENT OR IMAGING OF THE UTERUS

(75) Inventors: Michael P. H. Lau, Edmonds, WA (US); David P. Nelson, Snohomish, WA (US)

(73) Assignee: Mirabilis Medica Inc., Bothell, WA (US)

( * ) Notice: Subject to any disclaimer, the term of this patent is extended or adjusted under 35 U.S.C. 154(b) by 1402 days.

(21) Appl. No.: 12/641,248

(22) Filed: Dec. 17, 2009

Related U.S. Application Data (60) Provisional application No. 61/138,400, filed on Dec. 17, 2008.

(51) Int. Cl.
 *A61B 8/00* (2006.01)
 *A61B 17/00* (2006.01)
 *A61B 17/42* (2006.01)

(52) U.S. Cl.
 CPC ......... *A61B 17/00* (2013.01); *A61B 2017/4216* (2013.01)

(58) Field of Classification Search
 CPC .......................... A61B 2017/4216; A61B 8/40
 USPC ............................ 600/437, 439; 606/191–194
 See application file for complete search history.

(56) References Cited

U.S. PATENT DOCUMENTS

| | | |
|---|---|---|
| 3,470,868 A | 10/1969 | Krause |
| 3,480,002 A | 11/1969 | Flaherty |
| 3,676,584 A | 7/1972 | Plakas |
| 4,059,098 A | 11/1977 | Murdock |
| 4,097,835 A | 6/1978 | Green |
| 4,185,502 A | 1/1980 | Frank |
| 4,347,850 A | 9/1982 | Kelly-Fry |
| 4,484,569 A | 11/1984 | Driller |
| 4,742,829 A | 5/1988 | Law |
| 4,756,313 A | 7/1988 | Terwilliger |
| 4,817,616 A | 4/1989 | Goldstein |
| 4,858,613 A | 8/1989 | Fry |
| 4,893,624 A | 1/1990 | Lele |
| 4,932,414 A | 6/1990 | Coleman |
| 4,938,217 A | 7/1990 | Lele |

(Continued)

FOREIGN PATENT DOCUMENTS

| | | |
|---|---|---|
| JP | 05-23336 A | 2/1993 |
| JP | 2002-536040 A | 10/2002 |

OTHER PUBLICATIONS

Fennessy, F., A Review of Margnetic Resonance Imaging-Guided Focused Ultrasound Surgery of Uterine Fibroids, Top Magn Reason Imaging 2006; 17: 173-179.*

(Continued)

*Primary Examiner* — Rajeev Siripurapu
(74) *Attorney, Agent, or Firm* — Seed IP Law Group PLLC (57) ABSTRACT

A method and apparatus for treating uterine tissue with ultrasound energy. The method manipulates the position of the patient's uterus to decrease its distance from an ultrasound therapy transducer while simultaneously engaging a partially filled bladder such that the bladder is compressed to force any bowel tissue out of an acoustic window between the patient's abdominal wall and uterus. Ultrasound energy is then applied to the uterine tissue.

34 Claims, 10 Drawing Sheets

(56) References Cited

U.S. PATENT DOCUMENTS

| | | |
|---|---|---|
| 5,050,610 A | 9/1991 | Oaks |
| 5,492,126 A | 2/1996 | Hennige |
| 5,520,188 A | 5/1996 | Hennige |
| 5,882,302 A | 3/1999 | Driscoll, Jr. |
| 6,050,943 A | 4/2000 | Slayton |
| 6,068,653 A | 5/2000 | LaFontaine |
| 6,254,601 B1 | 7/2001 | Burbank |
| 6,425,867 B1 | 7/2002 | Vaezy |
| 6,451,013 B1 | 9/2002 | Bays |
| 6,602,251 B2 | 8/2003 | Burbank |
| 6,613,004 B1 | 9/2003 | Vitek |
| 6,676,601 B1 | 1/2004 | Lacoste |
| 6,692,450 B1 | 2/2004 | Coleman |
| 6,764,488 B1 | 7/2004 | Burbank |
| 6,840,936 B2 | 1/2005 | Sliwa, Jr. |
| 6,936,046 B2 | 8/2005 | Hissong |
| 7,070,565 B2 | 7/2006 | Vaezy |
| 7,090,643 B2 | 8/2006 | Fidel |
| 7,105,007 B2 | 9/2006 | Hibler |
| 7,297,116 B2 * | 11/2007 | Varghese et al. ............... 600/438 |
| 7,358,226 B2 | 4/2008 | Dayton |
| 7,470,241 B2 | 12/2008 | Weng |
| 7,591,794 B2 | 9/2009 | Lacoste |
| 7,686,763 B2 | 3/2010 | Vaezy |
| 2003/0018255 A1 * | 1/2003 | Martin et al. ................. 600/437 |
| 2003/0233045 A1 | 12/2003 | Vaezy |
| 2004/0082859 A1 | 4/2004 | Schaer |
| 2004/0152986 A1 | 8/2004 | Fidel |
| 2005/0038340 A1 * | 2/2005 | Vaezy et al. ................. 600/439 |
| 2005/0084538 A1 | 4/2005 | Dayton |
| 2005/0107702 A1 | 5/2005 | He |
| 2005/0149101 A1 * | 7/2005 | Huschmand Nia ........... 606/193 |
| 2005/0267454 A1 | 12/2005 | Hissong |
| 2006/0216275 A1 * | 9/2006 | Mon ............................ 424/93.2 |
| 2007/0066990 A1 | 3/2007 | Marsella |
| 2007/0071683 A1 | 3/2007 | Dayton |
| 2007/0194658 A1 | 8/2007 | Zhang |

OTHER PUBLICATIONS

Yoon, S., Patient selection guidelines in MR-guided focused ultrasound surgery of uterine fibroids: a pictorial guide to relevant findings in screening pelvic MRI, Eur Radiol (2008) 18: 2997-3006.*

Chen, L., et al., "Effect of Blood Perfusion on the Ablation of Liver Parenchyma With High-Intensity Focused Ultrasound," Physics in Medicine and Biology 38(11):1661-1673, Nov. 1993.

Cheng, S.-Q., et al., "High-Intensity Focused Ultrasound in the Treatment of Experimental Liver Tumour," Journal of Cancer Research and Clinical Oncology 123(4):219-223, Apr. 1997.

Delon-Martin, C., et al., "Venous Thrombosis Generation by Means of High-Intensity Focused Ultrasound," Ultrasound in Medicine & Biology 21(1):113-119, 1995.

Friedland, F., "Ultrasonic Therapy," American Journal of Nursing 59(9):1272-1275, Sep. 1959.

Fry, F.J., "Recent Bioeffects With Ultrasound on the Reproductive System and Solid Tumors," Journal of the Acoustical Society of America 63(Suppl. 1):S13, May 1978.

International Search Report and Written Opinion mailed May 11, 2010, issued in International Application No. PCT/US2009/059589, filed Oct. 5, 2009, 10 pages.

International Search Report and Written Opinion mailed Dec. 27, 2011, issued in International Application No. PCT/US2011/031129, 13 pages.

Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.

Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.

Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5 Pt. 1):953-1081, May 1995.

Ngo, F.C., et al., "An Experimental Analysis of a Sector-Vortex Phased Array Prototype," Proceedings of the IEEE Ultrasonics Symposium, Montreal, Oct. 3-6, 1989, vol. 2, pp. 999-1002.

Notice of Reasons for Rejection mailed Mar. 12, 2012, issued in Japanese Patent Application No. 2009-505639, filed Apr. 13, 2007, 7 pages.

Orsini-Meinhard, K., "UW Tech-Transfer Program Putting Discoveries to Work," The Seattle Times, May 27, 2007, 8 pages.

"ThermoDox™ Animal Studies to Be Presented at 6th International Symposium on Therapeutic Ultrasound in Oxford, England," Aug. 30-Sep. 2, 2006, Celsion, Inc.,<http://www.celsion.com/news/releasedetail.dfm> [retrieved Oct. 8, 2007], 2 pages.

"ThermoDox™: Heat-Activated Liposome Drug," © 2007 Celsion, Inc., <http://www.celsion.com/products/ThermoDox.cfm> [retrieved Oct. 8, 2007], 3 pages.

Umemura, S.-I., and C.A. Cain, "Acoustical Evaluation of a Prototype Sector-Vortex Phased-Array Applicator," IEEE Transactions on Ultrasonics, Ferroelectrics, and Frequency Control 39(1):32-38, Jan. 1992.

Vaezy, S., et al., "Image-Guided Acoustic Therapy," Annual Review of Biomedical Engineering 3:375-390, Aug. 2001.

Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.

* cited by examiner

ENGAGE

*Fig.4A.*

DISENGAGE

OPTIMIZATION OF ACOUSTIC WINDOW AND TARGET DEPTH FOR TRANSABDOMINAL ULTRASOUND TREATMENT OR IMAGING OF THE UTERUS

CROSS-REFERENCE TO RELATED APPLICATION

This application claims the benefit under 35 U.S.C. Section 119(e) of U.S. Provisional Application 61/138,400, filed Dec. 17, 2008, which is herein incorporated by reference in its entirety.

BACKGROUND

High intensity focused ultrasound (HIFU) can be used to treat various pathologies within the uterus. HIFU ablation of fibroids and adenomyosis have been reported, and various additional procedures may also be amenable to HIFU treatment, including endometrial ablation, ablation of polyps, et al.

When HIFU is applied transabdominally, it is important to ensure that the patient's bowel does not intervene in the beam path. Otherwise, the gas that is naturally present in bowel will tend to reflect the HIFU, resulting in reduced treatment efficacy and/or dangerous burns of the bowel tissue. If transabdominal imaging ultrasound is used to guide the HIFU treatment, bowel gas will tend to block its transmission as well, resulting in poor quality images of the uterus. The anatomical aperture through which ultrasound may pass safely and unimpeded by the bowel is herein termed the "acoustic window".

In addition, the target uterine tissue must remain within a treatable depth range, i.e. at a depth below the skin surface that is within the focal range of the HIFU and/or imaging transducers (which are typically limited by practical design considerations).

In an attempt to increase the acoustic window, users of commercially-available HIFU systems have reported catheterizing the patient's bladder and filling it with fluid to help displace bowel laterally away from the HIFU beam path. In doing so, the acoustic window becomes defined largely by the lateral dimensions of the bladder. Ultrasound is readily transmitted through the bladder (i.e. since the fluid is relatively transparent to ultrasound), but not through the surrounding bowel.

Yet as the bladder fills and expands laterally, it also tends to expand posteriorly away from the abdominal wall. This pushes the underlying uterus in the posterior direction as well, since the bowel and rectum behind the uterus tend to be easily compressed. As the uterus is pressed deeper by the filling bladder, it may eventually move out of range of the abdominally-placed ultrasound or HIFU transducer. Thus, filling the bladder can actually be counter-productive when used as a standalone technique for enlarging the acoustic window.

Furthermore, as the bladder fills, it assumes a more spherical shape and becomes less pliable. This results in a decreased contact area at the interfaces of the bladder-uterus and bladder-abdominal wall, allowing loops of bowel to slip in between these interfaces from the periphery.

Given these problems, there is a need for a technique that can reliably increase the size of the acoustic window by displacing the bowel from the intended beam path, while minimizing the required focal depth to reach uterine target tissue.

SUMMARY

Uterine manipulation is frequently performed to facilitate surgical intervention via open laparotomy or laparoscopy. Similarly, filling of the bladder is known to facilitate transabdominal ultrasound imaging, and has also been used to enlarge the acoustic window for HIFU treatment. The technology disclosed herein combines these techniques for the purposes of facilitating transabdominal ultrasound therapy or imaging. In one embodiment, transabdominal ultrasound is applied to the uterus for imaging and/or therapeutic purposes with the bladder at least partially filled and the uterus manipulated anteriorly such that it compresses and spreads the partially-filled bladder laterally in relation to the abdominal wall. The unexpectedly synergistic effect is to simultaneously enlarge the acoustic window AND reduce the depth of target uterine tissue—two highly desirable endpoints that have traditionally been considered to be at odds with one another.

In one preferred embodiment, the disclosed technology is uniquely suited to enable hand-guided HIFU treatment of uterine fibroids or other uterine pathologies in a cost-effective and convenient office setting.

In another embodiment a HIFU treatment system includes a control system that is programmed to change an amount of fluid that fills a bladder and/or to manipulate a patient's uterus in an anterior or posterior direction such that the size of the acoustic window is increased in order to deliver HIFU energy to a treatment area with the uterus.

In yet another embodiment, a number of uterine manipulators are disclosed that are made of materials that are designed to selectively absorb or reflect HIFU energy or to be transparent to HIFU energy.

This summary has introduced a few concepts in simplified form, but is not intended to identify all essential features or scope of the claimed subject matter. Certain aspects and advantages of one or more embodiments may be more readily appreciated by reference to the following description and drawings, which should be considered illustrative and not restrictive with regard to scope of the technology or claims.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

For purposes of this disclosure, the term "uterine tissue" should be considered to include any normal or pathological tissue within or connected to the uterus, including but not limited to myometrium, endometrium, cervix, serosa, fibroids, adenomyosis, polyps, et. al. The term "bowel" is meant to include small and large intestines. The term "HIFU" stands for "high intensity focused ultrasound", but should be considered interchangeable herein with the term "therapeutic ultrasound" (which is not necessarily focused). "Acoustic window" refers to the lateral dimensions of the path between the abdominal skin surface and the underlying uterus that is substantially free of obstacles to ultrasound transmission (including but not limited to the bowel). "Transabdominal" refers to the application of ultrasound from a probe placed on the skin of the abdomen. "Digital manipulation" refers to use of one or more fingers inserted transvaginally or transrectally to manipulate the position of the uterus or cervix.

Figure 1A:
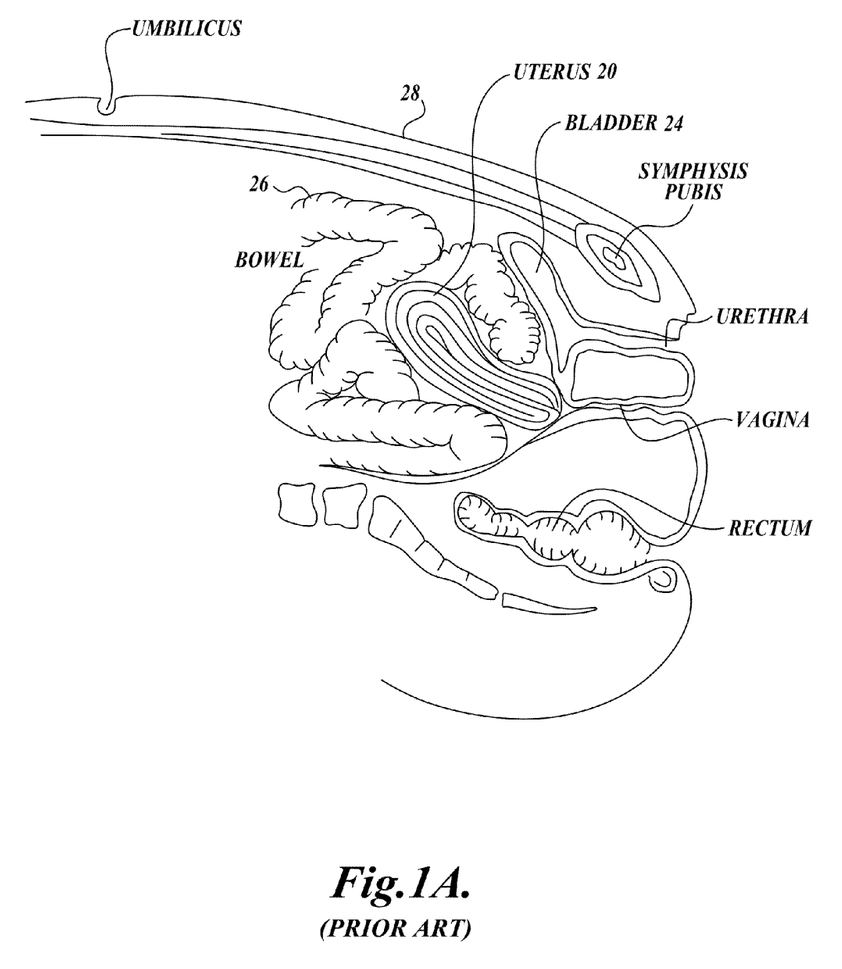
FIG. 1A illustrates a patient with an empty bladder and how a bowel section can be situated in the acoustic path between the abdomen and the uterus.

FIG. 1A illustrates a problem that the disclosed technology is designed to address. A patient requiring the application of HIFU to a target area in a uterus 20 has an empty or nearly empty bladder 24. Because the internal organs in the abdomen and pelvic cavity are soft and movable, portions of the patient's bowel 26 can move into the area between the abdomen 28, where a HIFU transducer will be placed, and the target area of the uterus 20. As indicated above, gas in the bowel can reflect HIFU energy in a manner that limits the treatment of the uterus and can cause potential burning of the bowel.

Figure 1B:
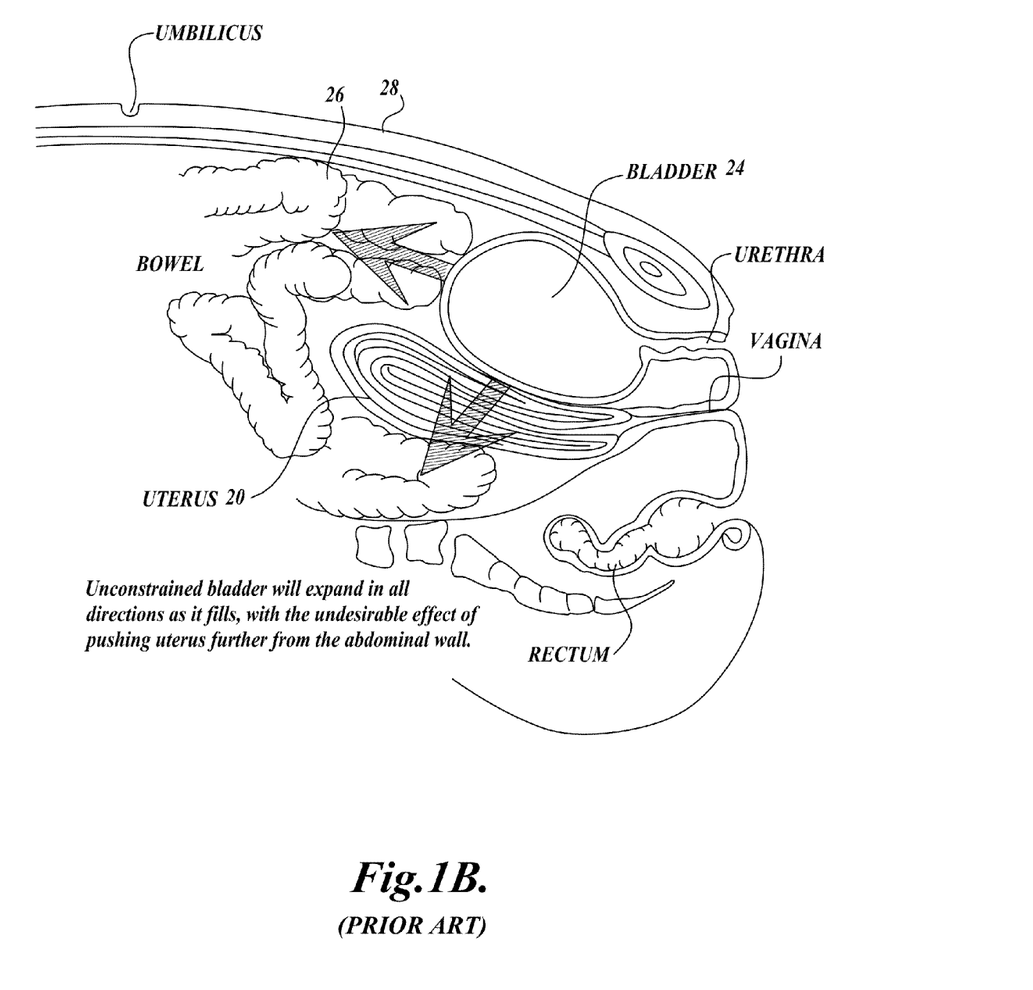
FIG. 1B illustrates a known technique for improving transabdominal ultrasound imaging, in which the bladder is filled to push the bowel laterally out of the acoustic path between the ultrasound transducer (placed on abdominal skin) and the underlying uterus.

FIG. 1B illustrates one conventional technique for improving transabdominal ultrasound imaging, in which the bladder 24 is naturally or artificially filled to push the bowel tissue 26 laterally out of the path between an ultrasound probe (not shown but would be placed on the abdominal skin) and the uterus 20. The bowel 26 typically contains gas which is highly reflective, and thus its presence in the ultrasound path can reduce imaging quality of the underlying uterus. In contrast, fluid in the bladder 24 is relatively transparent to ultrasound. However, this known technique comes with an undesirable side effect, i.e. as the bladder fills, the bladder expands posteriorly away from the abdomen 28 (as well as laterally), which pushes the uterus farther from the ultrasound probe and thereby tends to degrade image quality. Uterine depth is even more critical for HIFU treatment, given the practical limitations on HIFU focal range, which may prevent the ability to treat beyond a certain depth.

Figure 2:
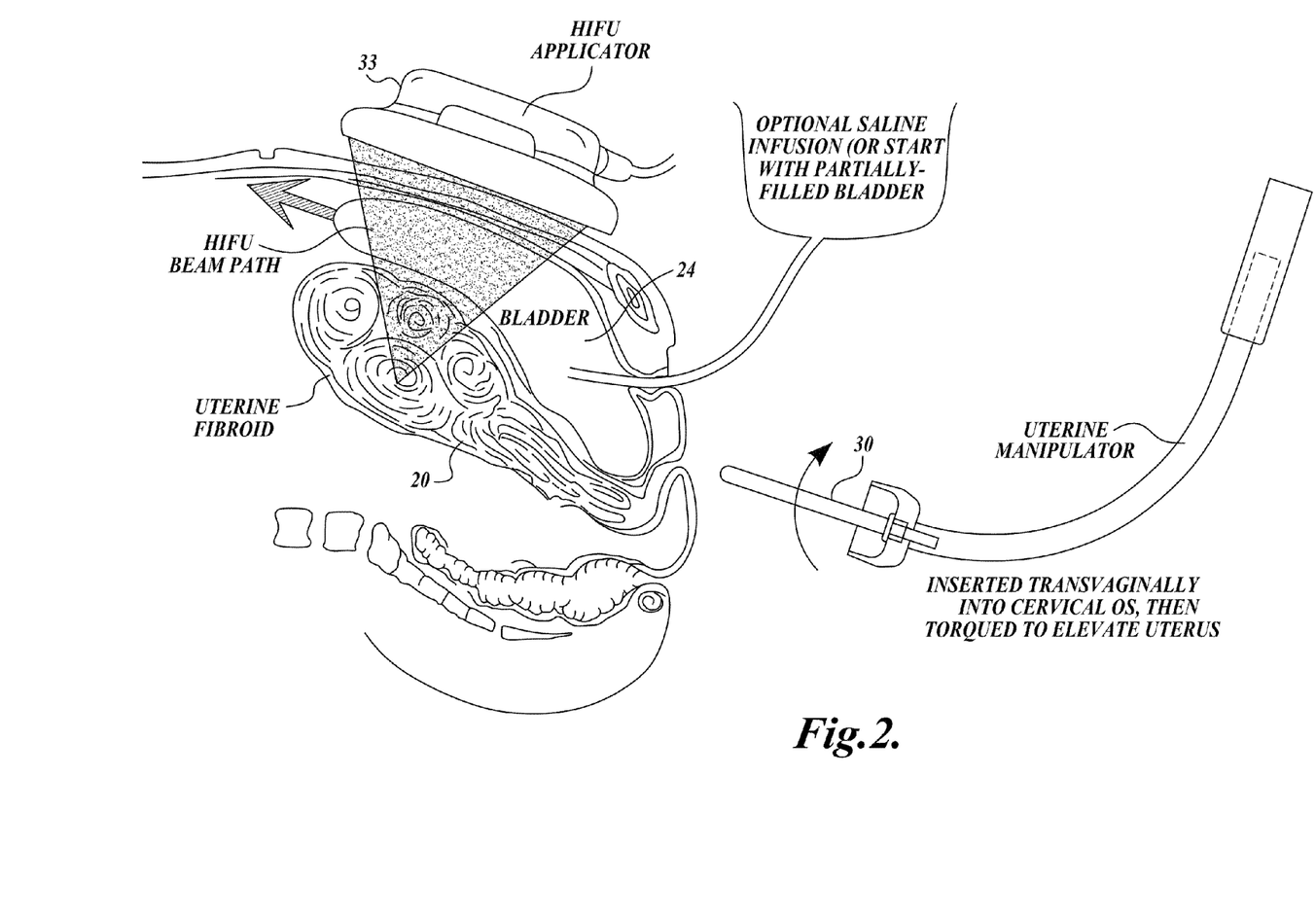
FIG. 2 shows one embodiment of the disclosed technology in which a uterine manipulator is inserted transcervically to press the uterus anteriorly into a partially filled bladder, thereby optimizing both the shape and size of the bladder.

FIG. 2 shows one embodiment of the disclosed technology in which a uterine manipulator 30 is inserted transcervically and manipulated to press the uterus 20 anteriorly into a partially filled bladder 24, thereby optimizing both the shape and size of the bladder 24. The bladder 24 is partially filled either naturally with urine or artificially by filling the bladder with saline or other liquid via a catheter. In some embodiments, a pressure monitor may be used to control an amount of liquid added to or removed from the bladder to maintain it at a desired level of fill. With the bladder 24 partially filled, the bladder is able to be compressed like a thick pancake by the uterus 20 that is moved with the uterine manipulator 30. The anterior compression of the uterus toward the abdominal wall causes the bladder to push any bowel tissue out of the way and increases the lateral width of the acoustic window, while simultaneously reducing the required focal depth to reach target tissue within the uterus 20.

Figure 3A:
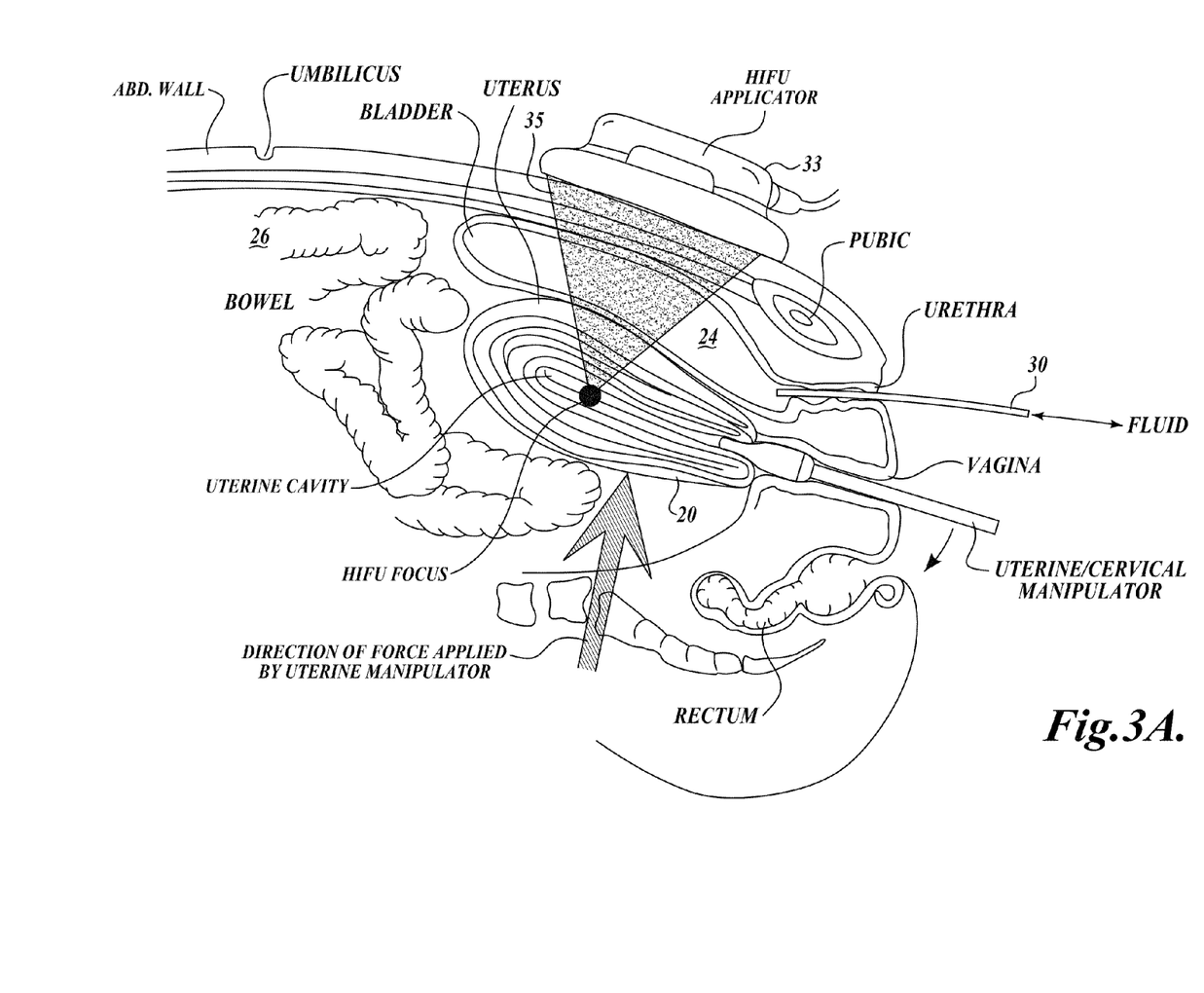
FIGS. 3A and 3B are sagittal and frontal views of an acoustic window created with one particular embodiment of the disclosed technology.
Figure 3B:
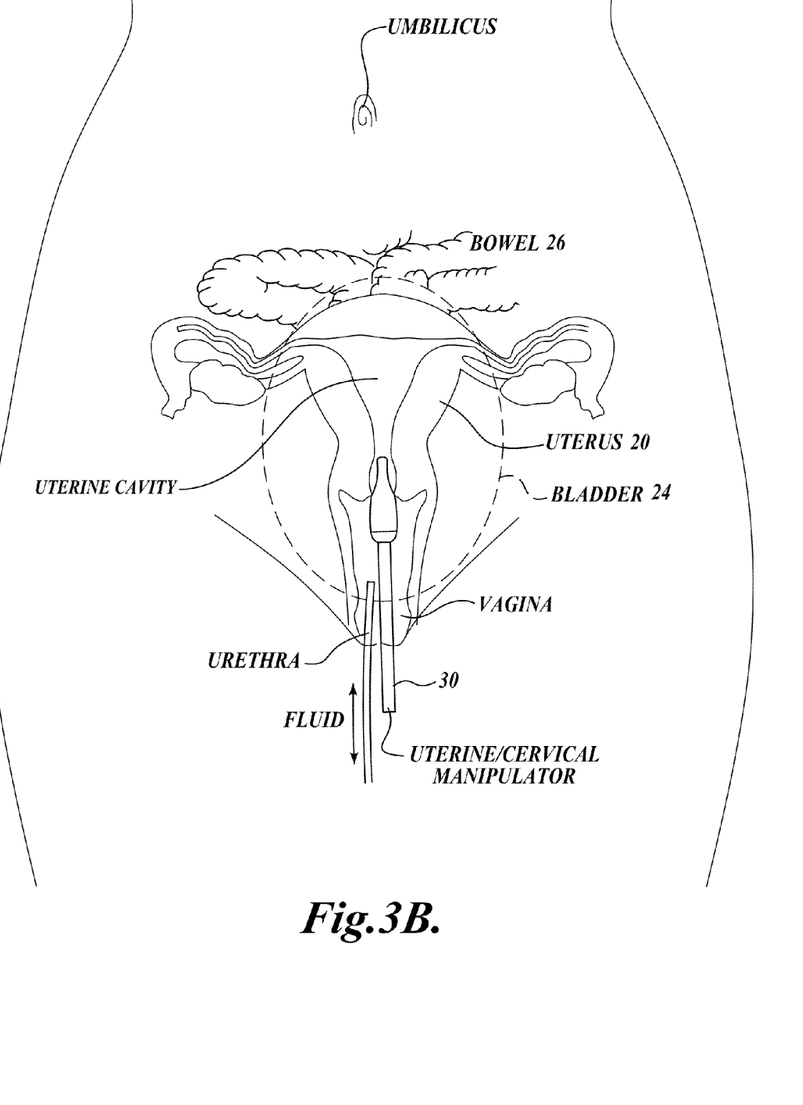

FIGS. 3A and 3B provides alternate sketches of the techniques disclosed herein, including sagittal and frontal views. The sagittal view shown in FIG. 3A illustrates how a patient's bowel 26 is moved laterally out of the way by the anterior compression of the uterus 20 into the partially filled bladder 24. As the bladder 24 is compressed, an acoustic window 35 created between the HIFU applicator 33 and a target treatment area in the uterus is free from bowel tissue. The frontal view shown in FIG. 3B illustrates how the uterus 20 is located directly posterior to the bladder 24, allowing the latter displace any bowel tissue that may be present between the HIFU applicator and the desired treatment area in the uterus.

Figure 4A:
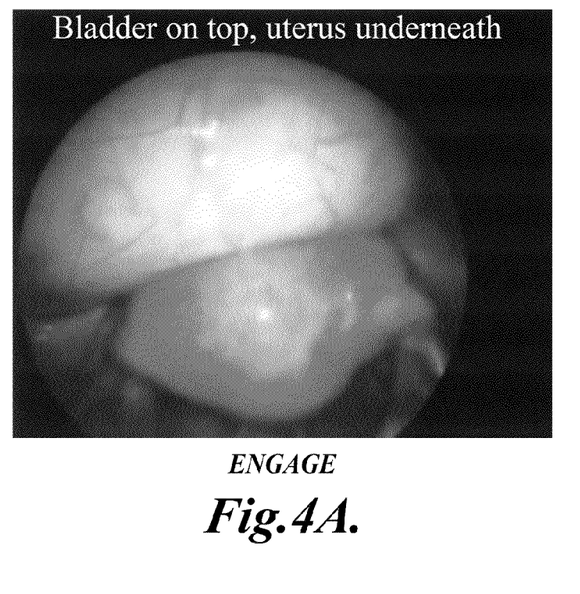
FIGS. 4A and 4B are laparoscopic photos that illustrate how elevation of the uterus allows it to push into the bladder, causing the latter to spread laterally and conform closely to the uterine surface.
Figure 4B:
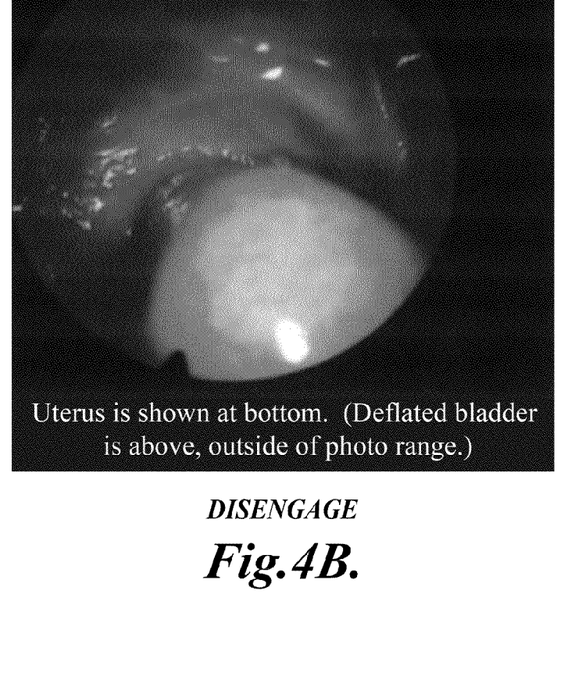

FIGS. 4A and 4B are laparoscopic photos to illustrate certain aspects of the disclosed technology. In the photo of FIG. 4B, the uterus is not manipulated and is not in contact with the overlying bladder. In the photo of FIG. 4A, a uterine manipulator (not shown) is used to elevate the uterus anteriorly into the bladder, causing the relatively pliable partially-filled bladder to conform to the anterior surface of the uterus. Although not shown in these photos, surrounding bowel would be pushed away by the resulting lateral expansion of the bladder.

One embodiment of the disclosed technology employs a transcervical element (solid or with hollow cannula for injecting fluid), with or without an atraumatic lip or lever arm that fits around or posterior to the cervix (e.g. in the posterior vaginal fornix) to aid in elevating the uterus. Such a design may eliminate the need for either an intracavitary element (which could interfere with HIFU transmission) or a tenaculum (which may cause pain and/or bleeding).

Alternatively, manipulation could be achieved via more conventional instruments which typically include some combination of: a transcervical element or cone, a cannula for injecting fluid into cavity, an intracavitary balloon, an articulating mechanism, and/or a tenaculum to help hold the transcervical element in position.

Such instrumentation may also be designed to lock the uterus in a desired position, thereby freeing the physician's hands for other purposes.

If transvaginal instrumentation is used to manipulate the uterus, it may or may not penetrate the cervical os. If it does so (e.g. a transcervical uterine manipulator), the instrumentation may or may not have a retaining balloon, which inflates inside the uterine cavity or cervical canal. The instrumentation may also have one or more portions (which may include a retaining balloon if present) that are specifically designed to reflect ultrasound energy, so as to facilitate visualization of its position during ultrasound imaging, serve as a point reflective source for time reversal correction of HIFU beam aberration, or aid in controlling HIFU effects in surrounding tissue. As will be explained in further detail below, the instrumentation may have one or more portions that are specifically designed to absorb ultrasound energy, so as to enhance the deposition of HIFU energy in surrounding tissue. Alternatively, the instrumentation may be designed with portions that are relatively transparent to ultrasound energy, so as to avoid affecting HIFU or ultrasound imaging.

In one embodiment, the instrumentation can have a retaining balloon that conforms to the uterine cavity and selectively absorbs HIFU energy to aid in ablating the endometrial lining. Such instrumentation may also be designed to be compatible with the use of MRI imaging (i.e. non-ferrous components), and could also be designed to enhance the instrumentation's visibility on MRI imaging. Such instrumentation (or attached balloons) may also include one or more temperature sensors to monitor surrounding tissue temperatures during HIFU treatment.

If transvaginal instrumentation is used to manipulate the uterus, it may also include a port for injecting fluid or gas into the uterine cavity and/or cervical canal. As a preferred embodiment, injection of a small amount of saline solution could be used if necessary to aid in visualization of the uterine cavity, e.g. to aid in targeting the endometrial lining and/or fibroids. However, such fluid or gas could also include compounds, particles or bubbles which reflect ultrasound, so as to facilitate visualization of the uterine cavity on ultrasound imaging and/or aid in controlling HIFU effects in surrounding tissue. Alternatively, such fluid or gas may include compounds, particles or bubbles which absorb ultrasound, so as to enhance the deposition of HIFU energy in surrounding tissue (including but not limited to the endometrial lining).

The uterus may be manipulated once at the beginning of a procedure, or its position may be adjusted intermittently or continually to aid in targeting of the ultrasound. This repositioning may be performed manually or automatically in response to various parameters.

In addition to upward pressure exerted on the uterus, counter compression may also be applied to the ultrasound applicator (on abdominal skin surface) to assist in optimizing the acoustic window and target tissue depth.

These techniques disclosed are preferably practiced with patient in a supine or seated position, with or without inclination of the torso to aid in shifting intestines out of the acoustic window. Such positions facilitate the use of HIFU to treat the uterus in a convenient low-cost office setting, since most gynecology offices already have examining tables which can accommodate such positions. However, the disclosed techniques may also be practiced with patient in prone or other positions.

In one embodiment, the bladder fill volume is chosen such that bladder can be compressed to minimal dimensions in the anterior-posterior direction, while maximizing its dimensions in the caudal-cephalic and side to side directions. The volume should also be kept low enough to maintain bladder pliability, so as to maximize the contact area between posterior abdominal wall and anterior bladder, and between posterior bladder and anterior uterus. This will exclude any intervening bowel between these surfaces and thus maximize the lateral dimensions of the acoustic window.

Bladder fill may be accomplished by a variety of techniques, including having patient arrive with a partially full bladder. If bladder is too full upon arrival, patient may void a measured amount, repeating this procedure until bladder reaches the desired size and degree of pliability. Alternatively, a catheter may be inserted into the bladder via the urethra to allow one-time or periodic addition or extraction of fluid from the bladder. In one embodiment, ongoing control of bladder volume may be accomplished via an indwelling catheter (with or without a retaining balloon).

Figure 5:
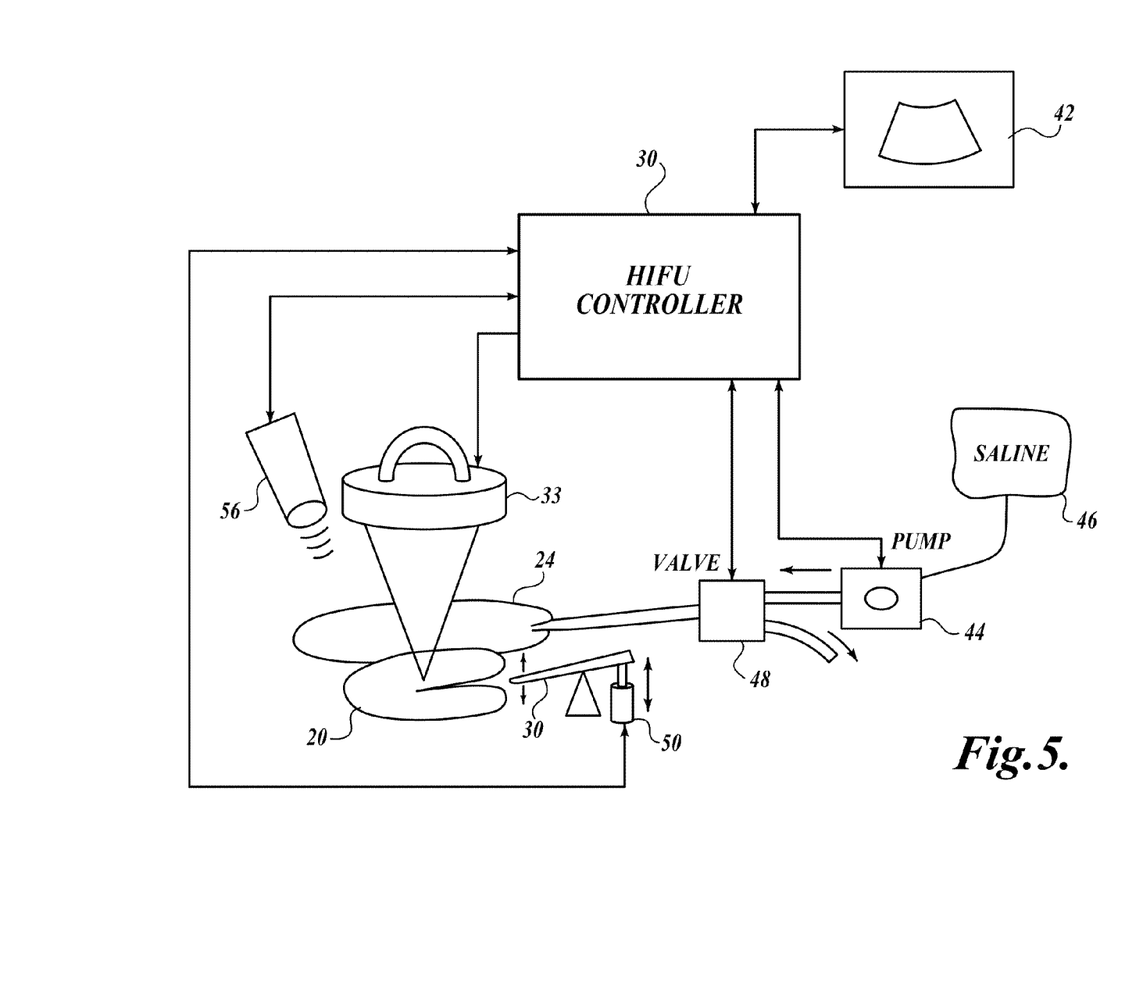
FIG. 5 illustrates a system for automatically controlling fluid delivered to or removed from a bladder and the position of a uterus to increase the size of the acoustic window in accordance with an embodiment of the disclosed technology.

FIG. 5 is a block diagram of a system for automatically controlling the fill of a bladder and the position of the uterus to optimize the acoustic window and treat the uterus with HIFU in accordance with the disclosed technology. In the embodiment shown, a HIFU controller 40 has hardware adapted to deliver HIFU energy though a HIFU transducer 33 to the patient. Images of the tissue being treated can be obtained either through imaging transducer elements on the HIFU transducer 33 or from a separate imaging transducer 56. The images of the tissue are displayed on a conventional ultrasound monitor 42.

The HIFU controller 40 controls the acoustic window through which HIFU energy is delivered to a uterus by selectively adding liquid to, or removing liquid from the patient's bladder 24. In the embodiment shown, the HIFU controller 40 controls a pump 44 that delivers liquid from a liquid source 46 into a catheter that is inserted into the bladder. The catheter can include a pressure sensor that produces signals read by a processor in the controller to monitor the liquid pressure in the bladder. To remove liquid from the bladder, the processor within controller 40 directs a valve 48 to be opened to allow liquid to drain from the bladder or closed to seal the liquid in the bladder. A uterine manipulator 30 is engaged with the uterus 20 and manipulated by a hydraulic piston, pneumatic cylinder, motor or a similar mechanism that controls the manipulator to move the uterus either in the anterior direction towards the bladder or in the posterior direction away from the bladder. As will be appreciated, movement towards the bladder compresses the bladder and pushes any bowel tissue out of the acoustic window 35. By adjusting the position of the uterus and the filling of the bladder, the HIFU controller 40 operates to remove bowel tissue from the acoustic window and reduces the depth required for the HIFU transducer 33 to treat the uterus 20. Note that, as an alternative to the uterine manipulator shown, the anterior/posterior position of the uterus with respect to HIFU applicator 33 could be adjusted by other methods including but not limited to: controlling the pressure on or vertical position of the applicator, or controlling the inflation of a rectal balloon.

In one embodiment, a processor within the controller 40 is programmed to analyze images obtained of the acoustic window. Any bright reflections around the periphery of the acoustic window or other reflections that may indicate that bowel tissue is in the acoustic window are detected. The HIFU controller 40 then adjusts either or both of the filling of the bladder and movement of the uterine manipulator to remove the source of reflections from the acoustic window. Continuous or intermittent control could be performed manually or automatically. The system can also set bladder fill volume in response to factors which might include (but are not limited to): position of and/or downward pressure exerted on the transabdominal applicator, position of and/or upward pressure exerted on the uterus, pressure within bladder, and location of target tissue relative to the ultrasound applicator.

In some cases, the uterus may be large enough to make direct contact with the abdominal wall everywhere within the intended HIFU beam path. In this case, there is no need to interpose the bladder, since direct contact would necessarily exclude the possibility of intervening bowel. To aid in establishing or maintaining a sufficiently large area of direct contact, the ultrasound applicator can be pressed down against the abdominal wall, and/or the uterus can be manipulated upward toward the abdominal wall.

In an alternative embodiment of the disclosed technology, manipulation of the uterus can be performed by a variety of techniques including digits (fingers) inserted transvaginally or transrectally, instruments placed in vaginal fornices or on the cervix and/or a transrectal instrument, enema or balloon. The techniques described herein will typically require only simple elevation of the uterus in an anterior direction (as opposed to surgical procedures which may require ability to manipulate the uterus more robustly and/or in multiple directions). Thus, the design of instrumentation to manipulate the uterus can be improved to be less traumatic or painful, thus minimizing the need for anesthesia during its insertion, manipulation or removal.

Figure 6A:
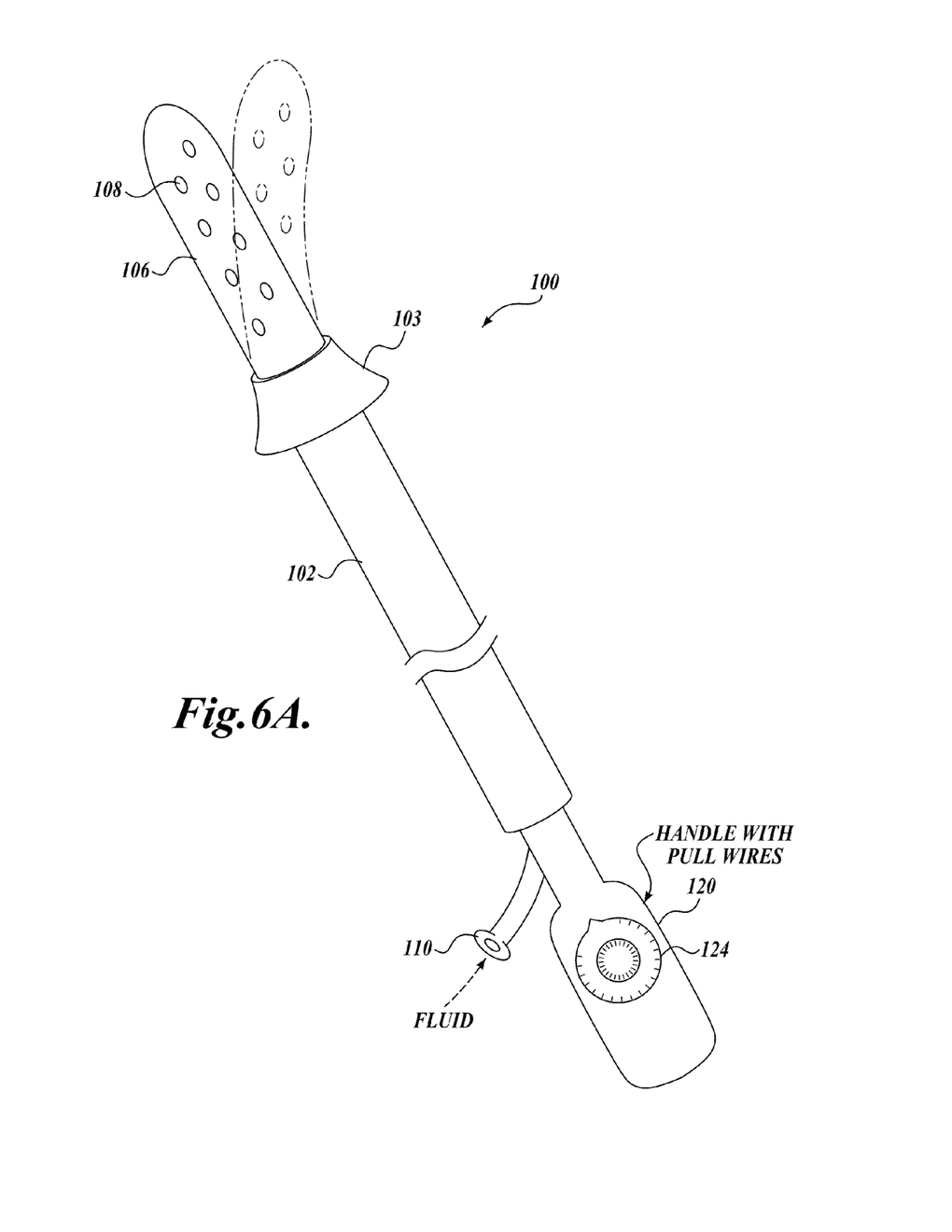
FIGS. 6A-6C illustrate uterine manipulators in accordance with embodiments of the disclosed technology.
Figure 6B:
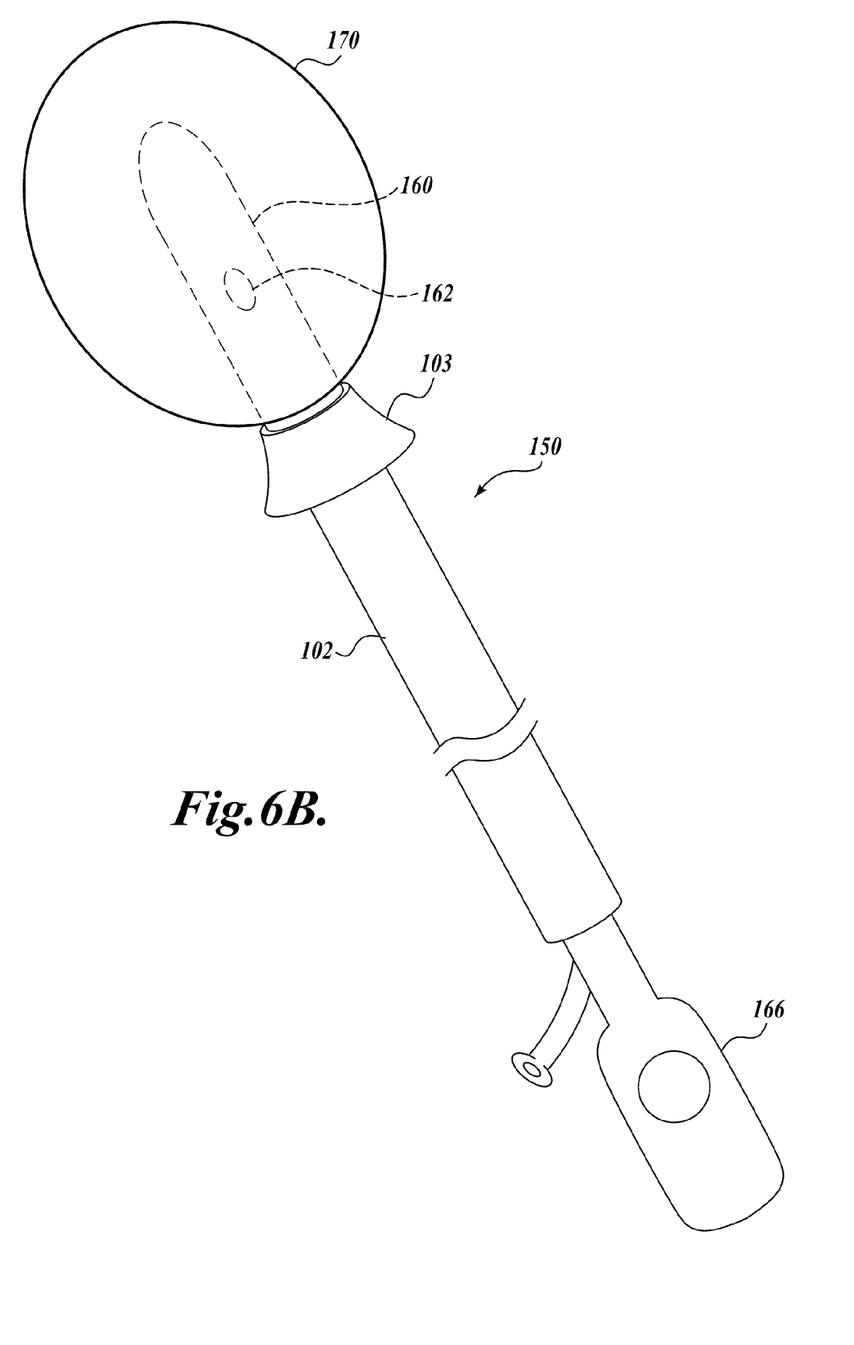
Figure 6C:
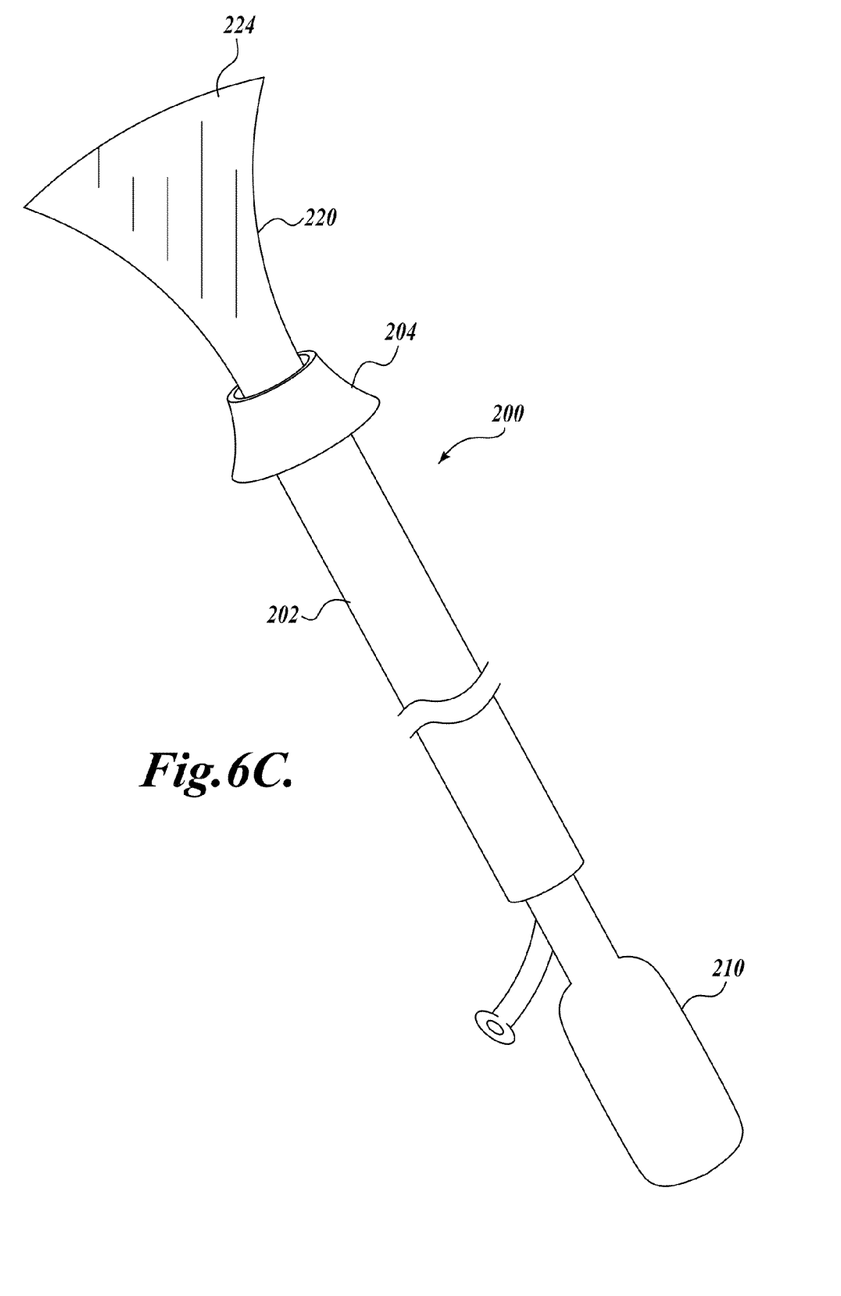

FIGS. 6A-6C illustrate a number of alternative embodiments of a uterine manipulator that are useful with the disclosed technology. In the embodiment shown in FIG. 6A, a uterine manipulator is designed to be substantially transparent to an applied HIFU beam. For example, if a patient has a uterine fibroid that is located on the backside (posterior) of the uterus, it is desirable that the uterine manipulator that is used to move the uterus does not impede the delivery of HIFU energy to the fibroid. As shown, a uterine manipulator 100 includes an outer sleeve 102 and an inner shaft 106 that can be advanced or retracted with respect to the outer sleeve. The distal end of the inner shaft 106 may include one or more ports 108 that are used for the delivery or extraction of fluids from the uterine cavity. Such fluids may aid visualization of the uterus during ultrasound imaging, or may be intended to cool the uterus or otherwise interact with HIFU to affect treatment of surrounding tissue, or may contain drugs to directly treat the uterine tissue. The ports 108 are in fluid communication with a fluid lumen (not shown) within the inner shaft that terminates at a fluid port 110. The distal end of the inner shaft may also include one or more sensors such as pressure sensors or temperature sensors produce signals that can be detected to inform the physician of conditions that are occurring in the uterus during treatment At the proximal end of the inner shaft 106 is a handle that includes controls to selectively tighten or relax controls wires within the inner shaft 106. The control wires are secured at their distal end to the distal end of the inner shaft such that tension on the controls wires cause the distal end of the shaft to bend in a desired direction in manner similar to a steerable catheter or endoscope. The inner shaft preferably includes an articulation joint near its distal end to aid in bending under tension of the control wires. Depending on the number of control wires and the configuration of the articulation joint, the distal tip of the inner shaft 106 can move in two or more directions. A flange 103 made of a biocompatible material (rubber etc.) is positioned at the distal end of the outer sleeve 102. During use, the flange 103 is engaged with the opening of the cervix and serves to aid in controlling uterine position as well as sealing the uterus to keep in any liquids.

The distal end of the inner shaft 106 is at least partially made of materials that are substantially transparent to HIFU energy. Such materials tend to match the acoustic impedance of the uterine tissue and have low acoustic attenuation with no specular or Rayleigh scatterers. Exemplary materials that exhibit good transparency to HIFU energy include cis-1,4 polybutadiene with ~0.5% peroxide linker available from Lanxess Corp., TPX (Polymethylpentene Copolymer) available from Mitsui Chemicals America; RTV-616 and RTV-630 (unloaded) available from Momentive Performance Materials (formerly GE Silicones); Castall U-2941 (Urethane; now relabeled as Circalok 6414) available from Lord Corp. In some cases a stiffening member, such as a stainless steel rod, may be included in the distal tip of the inner shaft to provide sufficient strength such that movement of the distal tip with the control wires can move and hold the uterus in the desired position. The stiffening member may be coupled to a heat sink or in thermal contact with liquids delivered from the ports 108 (or other cooling channels in the shaft) to prevent the rod from becoming excessively hot as HIFU energy is applied.

In some cases, it is desirable to thermally treat the endometrial lining of the uterus with heat caused by the application of HIFU. In this case, the uterine manipulator of the type shown in FIG. 6B can be used. In this embodiment, a uterine manipulator is at least partially constructed of material that is highly absorptive of HIFU. Absorptive materials have a good match to the acoustic impedance of tissue, yet high acoustic attenuation of HIFU and contain only low to moderate Rayleigh scatterers. Examples of such materials include but are not limited to Engage™ (Polyolefin Elastomer) available from Dow Chemical Co.; Surlyn™ (Thermoplastic Ionomer) available from DuPont; Santoprene™ (Thermoplastic Elastomer) available from ExxonMobil Chemical; RTV 560, 615, 630 with 5-10% by weight 25-50 µm borosilicate micro balloon available from Momentive Performance Materials (formerly GE Silicones). It may also be desirable to increase thermal conductivity by adding 5-15% by weight Al2O3, WO3 aluminum nitride and/or diamond powder.

In the embodiment shown in FIG. 6B, a uterine manipulator 150 has an outer sleeve 152 with a conical flange 153 at the distal end thereof that operates to stabilize the manipulator in relation to the uterus and to seal any liquids that may be delivered into the uterus. An inner shaft 160 is movable with respect to the outer sleeve 152 such that it can be inserted into or removed from the uterine cavity to a desired degree while the flange is engaged to the uterus. The inner shaft 160 may include one or more ports from which a liquid can be delivered to or withdrawn from the uterus. In some embodiments, the inner shaft 160 may include a handle 166 with controls for manipulating controls wires as described above. In this embodiment, the distal end of the inner shaft 160 includes a balloon 170 that is made of, or coated with, absorptive materials of the type described above. When inflated with a liquid or gas, the balloon 170 engages and conforms to the endometrial wall of the uterus. The application of HIFU energy when the balloon 170 is deployed causes the balloon to become heated in order to thermally treat the lining of the uterus.

In an alternative embodiment, the balloon 170 can be coated with, or made from, a material that is reflective of HIFU energy in order to reflect HIFU energy away from the center of the uterus. Examples of such reflective materials include stainless steel, aluminum, titanium or alumina To improve biocompatibility, it may be desirable to coat these materials with a thin jacket of a biocompatible material such as TPX or Santoprene.

In an alternative embodiment, the balloon itself may not be absorptive or reflective, but may be filled with fluid which is absorptive or reflective.

FIG. 6C illustrates yet another embodiment of a uterine manipulator. In this embodiment, a uterine manipulator 200 includes an outer shaft 202 with a conical flange 204 at the distal end. An inner shaft 210 is movable with respect to the outer shaft 202 such that a distal end of the inner shaft can be selectively inserted into and removed from a uterus. In this embodiment, the inner shaft has a number of support splines 220 that expand radially outwards when the inner shaft is pushed out of the distal end of the outer shaft 202. The support splines 220 support one or more sheets 224 of material that is absorptive or reflective of HIFU energy and are shaped to substantially fill the uterus when the support splines 220 are extended. In this embodiment, the support splines are sufficiently stiff such that force on the more proximal portions of the inner shaft 210 or the outer sleeve 202 can move and manipulate the position of the uterus.

With the one or more sheets of absorptive or reflective material deployed in the uterus, the application of HIFU energy will cause the sheets to heat or to reflect HIFU energy.

While illustrative embodiments have been illustrated and described, it will be appreciated that various changes can be made therein without departing from the scope of the invention. Those of ordinary skill in the art will understand that other embodiments fall within the scope of the description and the claims.

I claim:

1. A method of treating uterine tissue of a patient by way of transabdominal application of ultrasound energy, the method comprising:
    partially filling the patient's bladder with fluid either naturally or artificially;

manipulating the patient's uterus anteriorly such that it compresses the partially filled bladder to cause the bladder to spread laterally with respect to the patient's abdominal wall such that bowel tissue is pushed out of the way of an ultrasound beam path between the abdominal wall and the uterine tissue; and applying ultrasound energy through an acoustic window to the uterine tissue for treating the uterine tissue while the uterus remains compressed against the partially filled bladder, wherein the bladder is partially filled such that the bladder is compressible to minimize dimensions in the anterior-posterior direction, due to the manipulation of the patient's uterus, while simultaneously maximizing the bladder's dimensions in the caudal-cephalic and side to side directions.

2. The method of claim 1, wherein partially filling the patient's bladder creates sufficient bladder pliability to achieve maximal contact area between the posterior of the abdominal wall and the anterior of bladder, and between the posterior of the bladder and the anterior of the uterus.

3. The method of claim 1, wherein manipulating the patient's uterus is achieved by one or more of:
digital manipulation transvaginally;
an instrument placed in the vaginal fornices;
an instrument placed on a cervix;
a transcervical uterine and cervical manipulator; or
transrectal manipulation by digits, non-penetrating instruments, enema, or fluid-filled balloon placed in the rectum.

4. The method of claim 1, wherein the patient's uterus is manipulated by contacting the uterus with a uterine manipulator.

5. The method of claim 4, further comprising locking a position of the uterine manipulator prior to applying ultrasound energy to the uterine tissue.

6. The method of claim 4, wherein the uterine manipulator has at least one portion which reflects ultrasound energy.

7. The method of claim 4, wherein the uterine manipulator has at least one portion that is substantially transparent to ultrasound energy.

8. The method of claim 4, wherein the uterine manipulator has at least one portion that absorbs ultrasound energy.

9. The method of claim 4, wherein the uterine manipulator includes a retaining balloon that conforms to the uterine cavity and includes material designed to absorb ultrasound energy so as to aid in ablating an endometrial lining of the uterus.

10. The method of claim 4, wherein the uterine manipulator includes one or more ports for injecting fluid or gas into the uterine cavity and/or cervical canal.

11. The method of claim 4, wherein the uterine manipulator includes one or more thermal sensors.

12. The method of claim 4, wherein the uterine manipulator includes one or more pressure sensors.

13. The method of claim 1, wherein the uterus position is changed intermittently or continually during the application of ultrasound energy.

14. The method of claim 1, wherein the ultrasound energy is high intensity focused ultrasound (HIFU) energy.

15. The method of claim 14, wherein application of the HIFU energy is guided by real-time ultrasound imaging.

16. The method of claim 15, wherein the bladder is compressed by the uterine tissue such that the bladder pushes any bowel tissue out of the way of an entire HIFU beam path and increases a lateral width of the acoustic window.

17. The method of claim 1, wherein the bladder is partially filled by:
transferring fluid via a catheter to or from the bladder on a one-time or intermittent basis; or
continuously controlling the delivery of fluid to or from the bladder via an in-dwelling catheter.

18. The method of claim 17, further comprising controlling the partial filling of the patient's bladder so as to vary the size of the acoustic window, depth of target tissue, and/or location of ultrasound focus within the target tissue.

19. The method of claim 17, further comprising controlling a fill volume of the bladder in response to one or more of:
positioning and/or exerting downward pressure on the abdominal wall by a transabdominal ultrasound applicator;
positioning and/or exerting upward pressure on the uterus;
pressure within the bladder; and
a location of target tissue relative to the transabdominal ultrasound applicator.

20. The method of claim 1, further comprising applying counter compression via an ultrasound applicator on an abdominal skin surface to assist in optimizing the acoustic window and target tissue depth.

21. The method of claim 1, further comprising placing a patient in a supine, prone, or seated position to aid in shifting intestines out of the way of the ultrasound beam path.

22. A system for treating a patient's uterus with high intensity focused ultrasound (HIFU) energy, comprising:
a HIFU transducer that is controllable to deliver HIFU energy to the patient's uterus;
an imaging transducer for obtaining images of an area between the HIFU transducer and a target treatment area in the uterus; and
a controller including a processor that is programmed to control the filling of a liquid in the patient's bladder and to control a mechanism that adjusts an anterior/posterior position of the uterus with respect to the HIFU transducer in order to compress the bladder and displace any bowel tissue present in a HIFU beam path between the HIFU transducer and the target treatment area,
wherein the processor controls the filling of the liquid in the patient's bladder such that the bladder is compressible to minimize dimensions in the anterior-posterior direction, due to the adjustment of the anterior/posterior position of the uterus, while simultaneously maximizing the bladder's dimensions in the caudal-cephalic and side to side dimensions.

23. The system of claim 22, wherein the mechanism that adjusts the anterior/posterior position of the uterus comprises a uterine manipulator that is adapted to engage the uterus and be held in position under control of the processor such that the uterus compresses the bladder during delivery of HIFU energy from the HIFU transducer.

24. The system of claim 23, wherein the position of the uterine manipulator is locked prior to delivering HIFU energy to the patient's uterus.

25. The system of claim 23, wherein the uterine manipulator has at least one portion which reflects ultrasound energy.

26. The system of claim 23, wherein the uterine manipulator has at least one portion that is substantially transparent to ultrasound energy.

27. The system of claim 23, wherein the uterine manipulator has at least one portion that absorbs ultrasound energy.

28. The system of claim 23, wherein the uterine manipulator includes a retaining balloon that conforms to the uterine cavity and includes material designed to absorb ultrasound energy so as to aid in ablating an endometrial lining of the uterus.

29. The system of claim 23, wherein the uterine manipulator includes one or more ports for injecting fluid or gas into the uterine cavity and/or cervical canal.

30. The method of claim 22, wherein the position of the uterus is adjusted intermittently or continually during the delivery of HIFU energy.

31. The system of claim 22, wherein the bladder is compressed by the uterus such that the bladder pushes any bowel tissue out of the way of an entire HIFU beam path and increases a lateral width of an acoustic window for the HIFU beam path.

32. The system of claim 22, wherein the bladder is partially filled by:
    transferring liquid via a catheter to or from the bladder on a one-time or intermittent basis; or
    continuously controlling the delivery of liquid to or from the bladder via an in-dwelling catheter.

33. The system of claim 32, wherein the controller controls the partial filling of the patient's bladder so as to vary the size of an acoustic window, depth of target tissue, and/or location of ultrasound focus within the target treatment area.

34. The system of claim 32, wherein the controller controls a fill volume of the bladder in response to one or more of:
    positioning and/or exerting downward pressure on the abdominal wall by a transabdominal ultrasound applicator;
    positioning and/or exerting upward pressure on the uterus;
    pressure within the bladder; and
    a location of target tissue relative to the transabdominal ultrasound applicator.

* * * * *